United States Patent
Gelb et al.

(10) Patent No.: US 11,576,808 B2
(45) Date of Patent: Feb. 14, 2023

(54) APPARATUS AND KIT FOR AN ORAL APPLIANCE AND METHOD FOR USING SAME

(71) Applicants: Michael Gelb, Hartsdale, NY (US); Howard Hindin, Suffern, NY (US)

(72) Inventors: Michael Gelb, Hartsdale, NY (US); Howard Hindin, Suffern, NY (US)

(*) Notice: Subject to any disclaimer, the term of this patent is extended or adjusted under 35 U.S.C. 154(b) by 846 days.

(21) Appl. No.: 15/125,906

(22) PCT Filed: Mar. 18, 2015

(86) PCT No.: PCT/US2015/021266
§ 371 (c)(1),
(2) Date: Sep. 13, 2016

(87) PCT Pub. No.: WO2015/143043
PCT Pub. Date: Sep. 24, 2015

(65) Prior Publication Data
US 2017/0000643 A1    Jan. 5, 2017

Related U.S. Application Data

(60) Provisional application No. 61/955,274, filed on Mar. 19, 2014.

(51) Int. Cl.
*A61F 5/00* (2006.01)
*A61F 5/56* (2006.01)
(Continued)

(52) U.S. Cl.
CPC .............. *A61F 5/566* (2013.01); *A61C 7/08* (2013.01); *A61C 7/36* (2013.01)

(58) Field of Classification Search
CPC ... A61F 5/56; A61F 5/566; A61F 5/37; A61C 5/14; A61C 7/08; A61C 7/36; A63B 71/085
(Continued)

(56) References Cited

U.S. PATENT DOCUMENTS 5,427,117 A * 6/1995 Thornton ................ A61F 5/566
128/848
5,499,633 A    3/1996 Fenton
(Continued)

FOREIGN PATENT DOCUMENTS

WO    WO 2013-032884    3/2013

OTHER PUBLICATIONS

PCT/US2015/021266, International Preliminary Report on Patentability, dated Sep. 20, 2016, 6 pages—English.

*Primary Examiner* — Adam Baker
(74) *Attorney, Agent, or Firm* — Andrew F. Young, Esq.; Nolte Lackenbach Siegel

(57) ABSTRACT

An oral appliance and kit therefor is disclosed. The oral appliance may include generally U-shaped upper and lower body members and a pair of adjustment plates or spacers for removably connecting the upper body member with the lower body member. The generally U-shaped upper and lower body members are adapted to be positioned over at least a portion of first and second arches of teeth, respectively, with the spacers having a system of pins or pegs for adjustably repositioning the upper body member with respect to the lower body member. The upper and lower body members are further configured to provide a lingualless open space between the upper and lower body members to accommodate a tongue in a relaxed state. The disclosed oral appliance, system and kit therefor is configured for use in correcting the misalignment of a user's jaw.

21 Claims, 6 Drawing Sheets

(51) Int. Cl.
*A61C 7/36* (2006.01)
*A61C 7/08* (2006.01)

(58) Field of Classification Search
USPC .... 128/848, 859, 861, 862; 433/5–8, 19, 24, 433/140
See application file for complete search history.

(56) References Cited

U.S. PATENT DOCUMENTS

| | | | |
|---|---|---|---|
| 5,868,138 A | 2/1999 | Halstrom | |
| 7,178,529 B2 | 2/2007 | Kownacki | |
| 7,520,281 B1 | 4/2009 | Nahabedian | |
| 2008/0138766 A1* | 6/2008 | Jansheski | A61F 5/566 433/140 |
| 2008/0202530 A1* | 8/2008 | Sims | A61C 7/36 128/845 |
| 2011/0017220 A1* | 1/2011 | Lindsay | A61F 5/566 128/848 |
| 2013/0066236 A1* | 3/2013 | Herman | A63B 71/085 600/595 |
| 2013/0298916 A1* | 11/2013 | Alvarez | A61C 5/90 128/861 |
| 2014/0020691 A1* | 1/2014 | Sweeney | A61F 5/566 128/848 |
| 2014/0352701 A1* | 12/2014 | Ingemarsson-Matzen | A61F 5/566 128/848 |
| 2015/0173935 A1* | 6/2015 | Cooper | A61F 5/566 128/861 |

\* cited by examiner

APPARATUS AND KIT FOR AN ORAL APPLIANCE AND METHOD FOR USING SAME

CROSS REFERENCE TO RELATED APPLICATIONS

This application claims priority from and is a 371 National Phase of PCT/US15/021266 filed Mar. 18, 2015, which in turn claims priority from U.S. Ser. No. 61/955,274 filed Mar. 19, 2014 the entire contents of which are incorporated herein by reference.

FIGURE FOR PUBLICATION

FIG. 2

BACKGROUND OF THE INVENTION

Field of the Invention

The present invention generally relates to an oral appliance for corrective use, and more particularly to an oral appliance and kit therefor which includes generally U-shaped upper and lower body members and a pair of adjustment plates or spacers for removably connecting the upper body member with the lower body member. The generally U-shaped upper and lower body members are adapted to be positioned over at least a portion of a first or upper and a second or lower arches of teeth, respectively, with the spacers having a system of pins or pegs for adjustably repositioning the upper body member with respect to the lower body member. The upper and lower body members are further configured to provide a lingualless open space between the upper and lower body members to accommodate a tongue in a relaxed state The disclosed oral appliance, system and kit therefor is configured for use in correcting the relative misalignment of a user's jaw and improving the alignment of the users jaw and tongue and related anatomical structures for improving a patient or users airway, breathing, and physiological performance.

Snoring, sleep apnea, bruxism, TMD, TMJ, and the like may cause general discomfort, pain and compromised breathing and cause a poor night's sleep. Such ailments may also contribute to poor overall health. Sufferers of these conditions may sleep with tensed jaw muscles, which may in turn cause teeth, either upper or lower teeth to sit forward or rearward so that the jaws push the tongue base toward the rear of the oral cavity. The tongue based rearward movement may obstruct the oral and nasal airways.

Description of the Related Art

A person suffering from snoring, sleep apnea, bruxism, TMD, TMJ, and the like, teeth-grinding, or frequent awakenings and restless sleep generally clenches and grinds his/her teeth while sleeping. Such a person may experience a variety of unpleasant symptoms including, for example, headaches, stiff neck, receding gums, misshapen and misaligned teeth, worn teeth, sleeplessness, tempromandibular disease (TMD) and/or an irritated sleeping partner, to name a few.

A mouth guard or oral appliance is a protective or treatment device for the mouth that covers, in part, the teeth and gums to prevent and reduce injury to the teeth, arches, lips and gums. A mouthguard is most often used to prevent injury in contact sports, as a treatment for sleep apnea, bruxism, TMD, TMJ; and the like, or as part of certain dental procedures, such as tooth bleaching. Depending on application, it may also be called a mouth protector, mouth piece, gumshield, gumguard, nightguard, occlusal splint, bite splint, or bite plane.

Devices that sought to correct these conditions are known in the art. A person wears such a mouth guard device over his/her teeth while sleeping, or at other times. Forces generated due to the clenching and grinding of the teeth are then distributed to the guard rather than directly to the opposing teeth. Although such devices are typically worn over the top teeth, they also include devices worn over the bottom teeth or over both the top and bottom teeth. Generally, however, acquiring one of these oral guard devices requires multiple trips to the dentist over a period of a few weeks, at extremely high cost, and without flexibility between trips (e.g., inflexibility to a particular process). First, a person must visit his/her dentist so that a custom mold of his/her top teeth can be created. Next, the custom mold is sent to a laboratory where is used to create a custom-fit guard. The custom-fit tooth guard is typically made of a hard plastic and may or may not include embedded wires or prongs to ensure a snug fit. Upon completion, the custom-fit tooth guard is sent to the dentist. Subsequently, during a second visit, the custom-fit guard is fitted over the person's top teeth to determine if adjustments are needed. If adjustments are needed, the dentist, using a sanding means or chiseling means suitable for use with the hard plastic material, fine-tunes the exterior surface and/or the interior surface of custom-fit oral guard.

However, in addition to requiring multiple trips to the dentist, custom-fit oral guards may be considered costly by some and therefore unavailable to those of limited financial means. In addition, these guards typically need periodic replacement because as the plastic ages, the guards no longer fit or become uncomfortable to wear. In other cases, the person's teeth may shift or change due to age, an accident, braces or other factors. Such a shift or change may necessitate that their existing custom-fit night guard be redesigned and replaced, thereby requiring more time be spent at the dentist and adding further expense. Further, in addition to being somewhat messy, traditional custom-fit night guards encourage the proliferation and build-up of plaque and dental carries due to saliva build-up in their interior region while being worn.

Accordingly, this invention now recognizes that there is a need for an adjustable oral appliance that is convenient and that can provide correction of a retruded, retracted user's jaw in order to support a relaxed jaw, and an increased tongue space, and airway improvement in the mouth for reduced snoring, improved breathing during sleep or other activities.

SUMMARY OF THE INVENTION

An oral appliance and kit therefore is disclosed which includes generally U-shaped upper and lower body members and a pair of adjustment plates or spacers for removably connecting the upper body member with the lower body member. The generally U-shaped upper and lower body members are adapted to be positioned over at least a portion of first or top and second or bottom arches of teeth, respectively, with the spacers having a system of pins or pegs for adjustably repositioning the upper body member with respect to the lower body member. The upper and lower body members are further configured to provide a lingualless open space between the upper and lower body members to accommodate a tongue in a relaxed state. The disclosed oral appliance, system and kit therefor is configured for use in correcting the misalignment of a user's jaw. The device improves airway structure and function. With this improvement the tongue changes position, moves forward and counteracts gravity over time and in use for an improved airway structure and function.

The oral appliance disclosed herein improves on the prior art in a number of ways. Among other things, it is comfortable, it is inexpensive as compared to traditional custom-fit mouth guards, it does not require multiple trips to a dentist, it is readily adaptable to a person's specific mouth structure, is simple to use, and, in some cases, strategically placed padding on the oral appliance surfaces discourages grinding by applying subtle pressure to selected teeth. In addition, apertures formed in the disclosed oral appliance allow for the free flow of saliva, thereby mitigating the proliferation and build-up of plaque and dental concerns due to saliva accumulation around the teeth while being worn.

In summary, the oral appliance disclosed herein includes first and second generally U-shaped body members adapted to be positioned over at least a portion of first and second arches of teeth, wherein said upper and lower body members each have a plurality of connecting holes on a contact surface thereof; and at least a pair of repositionable spacing elements removably disposed on said contact surface of each of said first and second U-shaped body members proximate to a location of canine teeth and posteriorly of the first and second arches of teeth, wherein said spacing elements further comprise a generally flat base plate, a plurality of connecting pegs positioned on each of a first and second side of said base plate and projecting a distance from said base plate, and a side latching element configured at an angle with respect to said base plate.

In another aspect, an exterior surface of each of the first and second U-shaped body members comprises the generally horizontal contact surface contiguously coupled to first and second generally vertical side surfaces forming an interior channel therein, wherein the first vertical side surface is adapted to correspond to a front surface of one of the first or second arches of teeth and the second vertical side surface is adapted to correspond to a back surface of the first or second arches of teeth, the interior channel of the U-shaped body generally conforming to a shape of the first or second arches of teeth. The plurality of holes may be adapted to removably receive at least one of the connecting pegs. A portion of the first and second U-shaped body members comprises a material selected from the group consisting of a flexible polymeric material, a flexible ethylene material, a rigid polymeric material, and a polymerizable acrylic compound, or may be a material that is capable of being molded to conform to a shape of a dental arch of a patient with the application of heat, or a flexible heat responsive polymeric material that shapes to a user's first or second arch of teeth in response to heating and then cooling the U-shaped body member.

In another embodiment, an oral appliance is provided that comprises: first and second generally U-shaped body members adapted to be positioned over at least a portion of first and second arches of teeth, wherein each of said body members comprises a portion of rigid material and a portion of flexible material; and at least one adjustment plate having at least two connecting pegs for repositionably connecting opposing surfaces of said first and second body members. An exterior surface of each of the first and second U-shaped body members comprises the contact surfaces contiguously coupled first and second generally vertical side surfaces forming an interior channel therein, wherein the first vertical side surface is adapted to correspond to a front surface of one of the first or second arches of teeth and the second vertical side surface is adapted to correspond to a back surface of the first or second arches of teeth, the interior channel of the U-shaped body generally conforming to a shape of the first or second arches of teeth, and wherein said contact surfaces are connected with the at least one adjustment plate. Each of the plurality of holes may be adapted to removably receive at least one of the connecting pegs. A portion of the first and second U-shaped body members may comprise a material selected from the group consisting of a flexible polymeric material, a flexible ethylene material, a polymerizable acrylic compound, and a rigid polymeric material, or a material that is capable of being molded to conform to a shape of a dental arch of a patient with the application of heat, or a flexible heat responsive polymeric material that shapes to a user's first or second arch of teeth in response to heating and then cooling the U-shaped body member.

The embodiments of the oral appliance may have dimensions such that the first or second body member has a lateral width in the range of about 1 inch and about 2.5 inches, a longitudinal length in the range of about 2 inch and about 3 inches, and a height thickness in the range of about 0.25 inch and about 0.75 inch. Preferably, the first or second body member has a lateral width of about 1.75 inches, a longitudinal length of about 2.5 inches, and a height thickness of about 0.5 inch or of about 0.65 inch. Also preferably, the oral appliance comprises a plurality of pairs of adjustment plates, each pair of adjustment plates comprising connecting pegs positioned in different locations on said base plates.

In another aspect of the present invention, a kit for providing an oral appliance for correcting misalignment of a user's teeth or jaw to alleviating tension and/or stress is provided comprising: a storage container having a plurality of cavities for housing an oral appliance; first and second generally U-shaped body members of said oral appliance; and a plurality of pairs of adjustment plates or spacers stored in a visibly accessible manner. The generally U-shaped body members in the kit have opposing upper and lower planar surfaces, an inner surface and outer surface, the body members comprising a material that is capable of being molded to conform to a shape of a dental arch of a patient with the application of heat, and comprise a material selected from the group consisting of a flexible polymeric material, a flexible ethylene material, a rigid polymeric material, and a polymerizable acrylic compound.

In another aspect of the present invention, a method for correcting misalignment of a user's teeth or jaw to alleviating tension and/or stress is provided, wherein the method comprising the steps of: providing an oral appliance having first and second generally U-shaped body members adapted to be positioned over at least a portion of first and second arches of teeth, and first and second adjustment plates each having at least two connecting pegs on each of a first and second side thereof; connecting opposing contact surfaces of said first and second body members with said first adjustment plate; placing said oral appliance between upper and lower teeth of a user; removing said oral appliance from said upper and lower teeth of a user; disconnecting said opposing contact surfaces of said first and second body members from said first adjustment plate; connecting opposing contact surfaces of said first and second body members with said second adjustment plate to form a second oral appliance; and placing said second oral appliance between upper and lower teeth of a user; wherein at least one of said connecting pegs on said first adjustment plate is in different position from at least one of said connecting pegs on said second adjustment plate.

In still other aspects of the present invention, the oral appliance is configured for use as an adjustable over the counter sleep appliance using the specialized tabs.

In still other aspects of the present invention, the oral appliance is configured for use as an in office provisional appliance by the dental professional.

In still other aspects of the present invention, the oral appliance is configured for use as a trial sleep appliance.

In still other aspects of the present invention, the oral appliance is configured for use as a bite registration for the dental professional to fabricate a lab appliance.

In still other aspects of the present invention, the oral appliance is configured for use as an upper/lower appliance for treatment of bruxism, TMD, orofacial pain, and the like, using the supplied vertical tabs with soft occlusal indexing.

In still other aspects of the present invention, the oral appliance is configured for use as an upper and/or lower sports appliance using the included vertical tabs.

In still other aspects of the present invention, the oral appliance is configured for use in a sleep lab as a mandibular advancement appliance or prototype to fabricate a MA appliance.

In still other aspects of the present invention, the oral appliance is configured for use to register the occlusion for a prosthetic reconstruction.

In still other aspects of the present invention, the oral appliance is configured for use as a bruxism (TMD) appliance with anterior discluding ramp to be worn with upper and lower at the same time.

In still other aspects of the present invention, the oral appliance is configured for use as a 3D printable device with holes.

In still other aspects of the present invention, the oral appliance is configured for use as a jaw repositioning appliance in conjunction with physiological monitoring to determine the physiological position for sleep/TMJ treatment and restorative dental treatment.

In still other aspects of the present invention, the oral appliance is configured for use as an emergency seizure device.

In still other aspects of the present invention, the oral appliance is configured for use as an autophagical device.

In still other aspects of the present invention, the oral appliance is configured for use as a dual sports appliance.

In still other aspects of the present invention, the oral appliance is configured for use as dental impression trays.

In still other aspects of the present invention, the oral appliance is configured for use as multi-colored (including clear) device describing the above applications.

In still other aspects of the present invention, the oral appliance is configured for use as a myofunctional trainer.

In still other aspects of the present invention, the oral appliance is configured for use as orthodontic retention.

The above and other aspects, features and advantages of the present invention will become apparent from the following description read in conjunction with the accompanying drawings, in which like reference numerals designate the same elements.

BRIEF DESCRIPTION OF THE DRAWINGS

A further understanding of the present invention can be obtained by reference to a preferred embodiment set forth in the illustrations of the accompanying drawings. Although the illustrated preferred embodiment is merely exemplary of methods, structures and compositions for carrying out the present invention, both the organization and method of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the present invention, reference is now made to the following drawings in which.

DETAILED DESCRIPTION OF THE PREFERRED EMBODIMENTS

Figure 1:
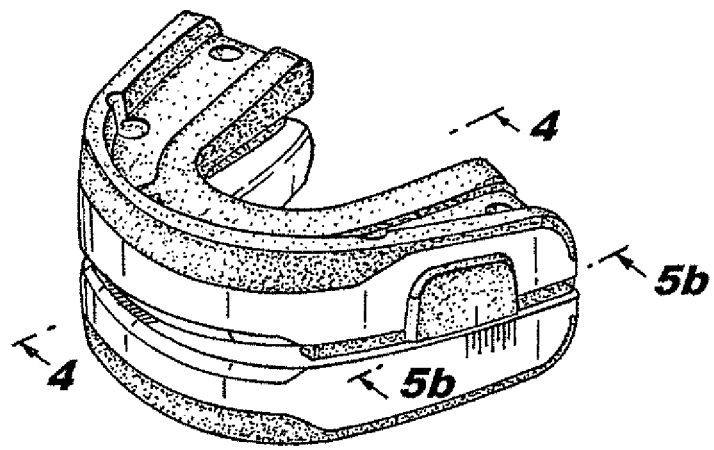
FIG. 1 shows a front perspective view of an oral appliance in accordance with an exemplary embodiment of the present invention.
Figure 2:
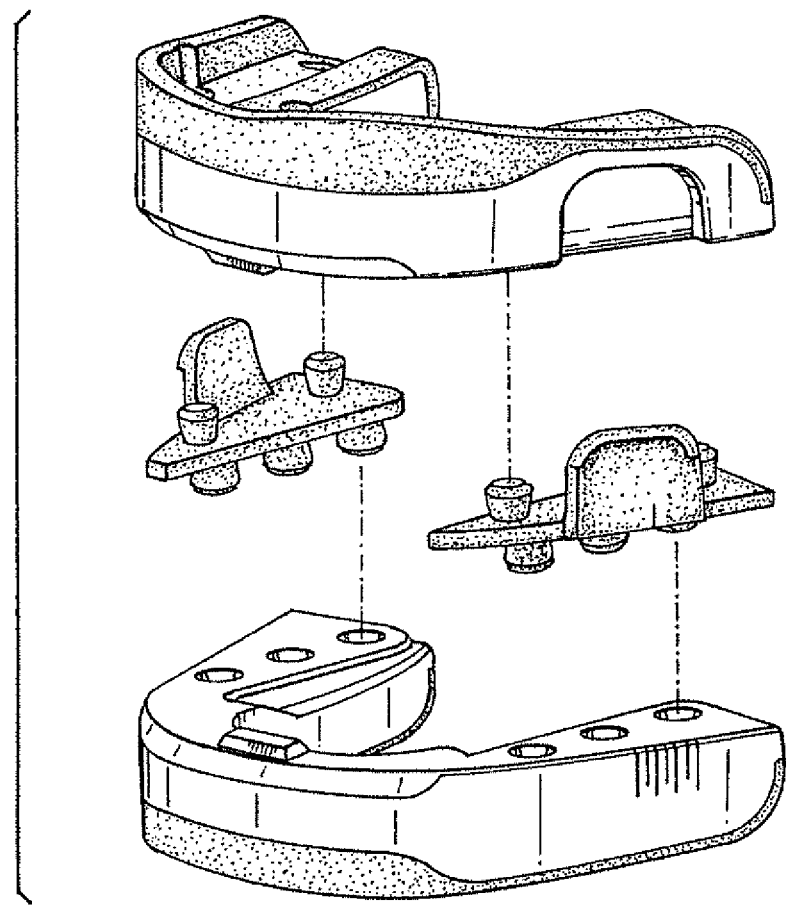
FIG. 2 shows a front exploded perspective view of the oral appliance shown in FIG. 1.
Figure 3:
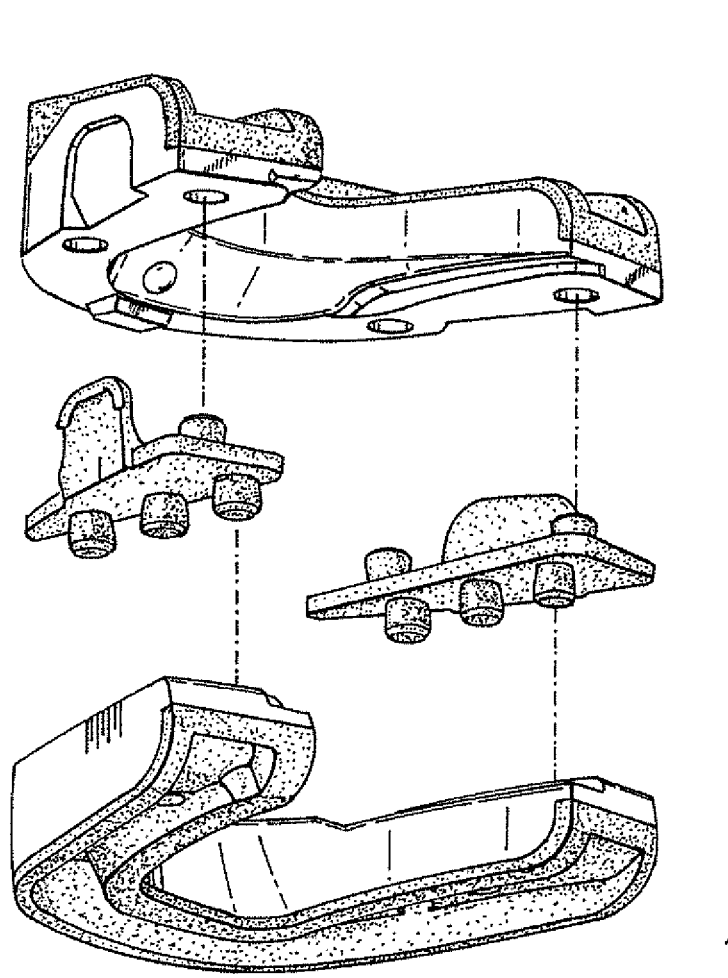
FIG. 3 shows a rear exploded perspective view of the oral appliance shown in FIG. 1.
Figure 4:
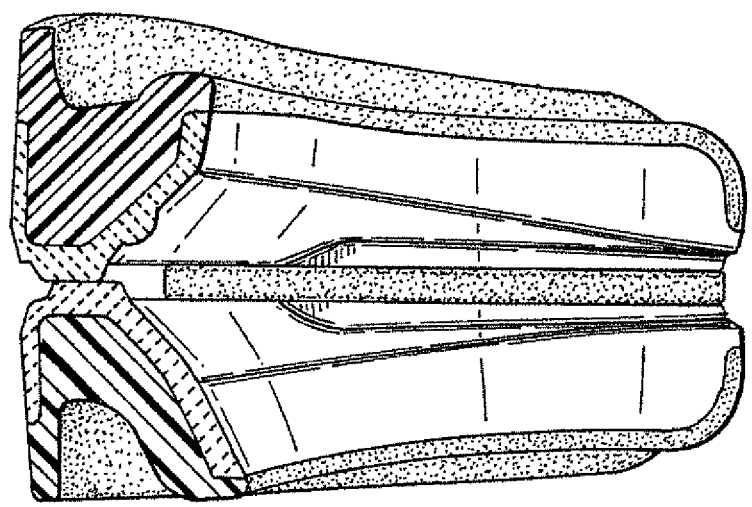
FIG. 4 shows a side cross-sectional view of the oral appliance of FIG. 1 taken along line 4-4.

As required, a detailed illustrative embodiment of the present invention is disclosed herein. However, techniques, systems, compositions and operating structures in accordance with the present invention may be embodied in a wide variety of sizes, shapes, forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein which define the scope of the present invention.

Reference will now be made in detail to several embodiments of the invention that are illustrated in the accompanying drawings. Wherever possible, same or similar reference numerals are used in the drawings and the description to refer to the same or like parts or steps. The drawings are in simplified forma and are not to precise scale. For purposes of convenience and clarity only, directional terms, such as top, bottom, up, down, over, above, below, etc., or motional terms, such as forward, back, sideways, transverse, etc. may be used with respect to the drawings. These and similar directional terms should not be construed to limit the scope of the invention in any manner.

Referring first to FIGS. 1-4, shown are various views of one exemplary embodiment of an oral appliance 10 constructed in accordance with this invention. As will be described in more detail below, the oral appliance 10 disclosed herein includes first and second generally U-shaped body members 12*a*/12*b* adapted to be positioned over at least a portion of first and second arches of teeth. The upper and lower body members 12*a*/12*b* each have a plurality of connecting holes 20*a*/20*b* on a contact surface thereof. At least a pair of repositionable spacing elements 14*a*/14*b* are provided that may be removably disposed on the contact surface of each of the first and second body members 12*a*/12*b*.

Preferably, the spacers 14a/14b are positionable proximate to a location of a user's canine teeth of each of the first and second arches. The spacing elements 14a/14b further comprise a generally flat base plate 15a/15b, a plurality of connecting pegs 18a/18b positioned on each of a first and second side of the base plate 15a/15b and projecting outward a distance from the base plate 15a/15b. While only two or three connecting pegs 18a/18b are depicted, any number of pegs 18a/18b may be used in accordance with the invention. Also, each of spacers 14a/14b preferably has stiffening/latching side elements 16a/16b protruding upward at an angle from an edge of the base plates 15a/15b. Side latching element 16a/16b is preferably configured at an angle with respect to the base plate 15a/15b and has a lip 17a/17b for engaging a corresponding recess in a side wall 6 of the upper or lower body member 12a/12b. Also, it is preferred that each spacer 14a/14b further include marking indicia 1, preferably located on an outer side of the protruding side element 16a/16b so as to correspond to similar marking indicia 2 on a side wall of upper or lower body members 12a/12b. The purpose of these marking indicia ½ is to allow the user or dental practitioner to assess the progression from use of the oral appliance 10.

Preferably, opposing upper and lower front spacing protrusions 22a/22b are provided on each contact surface of the upper and lower body members 12a/12b. Spacing protrusions 22a/22b are preferably configured so as to rest against one another upon assembly of the oral appliance 10. Also, spacing protrusions 22a/22b are sized so as to allow a front air gap 5 between a front region of upper and lower body members 12a/12b.

In another aspect, an exterior surface of each of the first and second U-shaped body members 12a/12b comprises the generally horizontal contact surface contiguously coupled to first and second generally vertical side surfaces to form an interior channel 13a/13b. Here, the first vertical side surface corresponds to a front or outer surface of the first or second arches of teeth and the second vertical side surface corresponds to a back or inner surface of the first or second arches of teeth. The interior channels 13a/13b of the U-shaped body generally conforms to a shape of the first or second arches of a user's teeth and comprises the softening material 4 for molding to the shape and size of the user's teeth. The plurality of holes 20a/20b may be adapted to removably receive at least one of the connecting pegs 18a/18b.

Preferably, a portion of the first and second U-shaped body members 12a/12b comprises both a rigid portion 3 and a softening portion 4. The softening portion 4 is provided so as to be able to mold or custom fit the oral appliance 10 to an individual user. It is also preferred that the materials used are selected from the group consisting of a flexible polymeric material, a flexible ethylene material, a rigid polymeric material, and a polymerizable acrylic compound. Alternatively, any material may be used that is capable of being molded to conform to a shape of a dental arch of a patient with the application of heat. Still alternatively a flexible heat responsive polymeric material that shapes to a user's first or second arch of teeth in response to heating and then cooling the U-shaped body member may be used.

In still another embodiment, the oral appliance 10 comprises first and second generally U-shaped body members 12a/12b adapted to be positioned over at least a portion of first and second arches of teeth. Each of the body members 12a/12b comprises a portion of rigid material 3 and a portion of flexible material 4. At least one adjustment plate 14a/14b having at least two connecting pegs 18a/18b for repositionable connection of opposing surfaces of the first and second body members 12a/12b is provided. Each of the plurality of holes 20a/20b may be adapted to removably receive at least one of the connecting pegs 18a/18b. The holes 20a/20b and pegs 18a/18b may be formed in one of any number of suitable shapes such as slits or circular holes, to name a few. An exterior surface of each of the first and second U-shaped body members 12a/12b comprises the contact surfaces contiguously coupled first and second generally vertical side surfaces forming the interior channel 13a/13b. Also, the generally vertical side surfaces of the body members 12a/12b are configured so as to form on an inner region 7a/7b of the oral appliance 10 an angled inner surface 8a/8b for the proper positioning of the user's tongue during use of the oral appliance 10 so as to not interfere with the user's breathing. Optionally, a tongue training reflex contact 21 may be provided generally near the inner front wall surface of the oral appliance 10, which is a training function, and results in relaxed tongue for easier swallowing . . . Such an device 21 is configured to train or encourage the tongue to rest or lie naturally in a specific position.

In accordance with the invention, the oral appliance 10 may be provided in various sizes such as youth, adult, small, medium, large, etc. However, preferred embodiments of the oral appliance 10 according to the invention may have dimensions such that the first or second body member 12a/12b has a lateral width in the range of about 1 inch and about 2.5 inches, a longitudinal length in the range of about 2 inch and about 3 inches, and a height thickness in the range of about 0.25 inch and about 0.75 inch. Preferably, the first or second body member 12a/12b has a lateral width of about 1.75 inches, a longitudinal length of about 2.5 inches, and a height thickness of about 0.5 inch or of about 0.65 inch. Also preferably, the oral appliance 10 comprises a plurality of pairs of adjustment plates 14a/14b, each pair of adjustment plates comprising connecting pegs 18a/18b positioned in different locations on the base plates 15a/15b.

Although only a pair of adjustment plates 14a/14b are shown and described, it is contemplated that other plate arrangements may be utilized in connection with the U-shaped body 12a/12b of oral appliance 10. For example, appliance 10 may have pegs/holes formed therein in accordance with different shapes, sizes and numbers. Also, the placement of the plates 14a/14b may be varied with respect to the individual teeth of the user, depending on the selected design of the oral appliance 10. Similarly, the positioning of and distances between each of the holes 20a/20b and pegs 18a/18b may be varied, depending on selected design of the oral appliance 10.

Figure 5A:
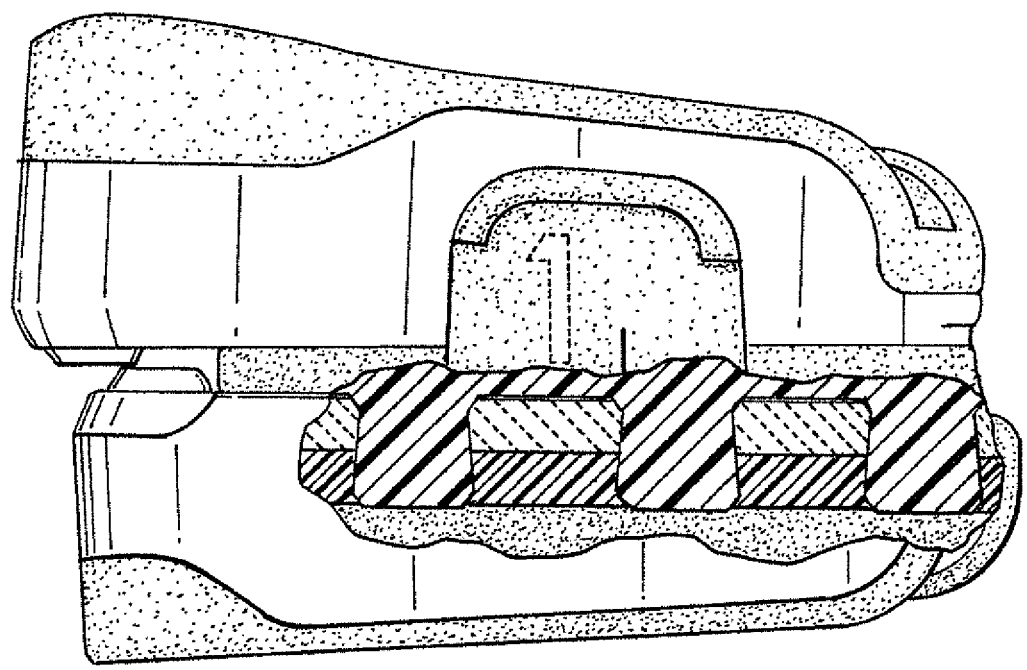
FIGS. 5*a-c* show partial cut-away side views of the oral appliance shown in FIG. 1 depicted in each of a first, second and third configuration showing a progression of overbite orientations.
Figure 5B:
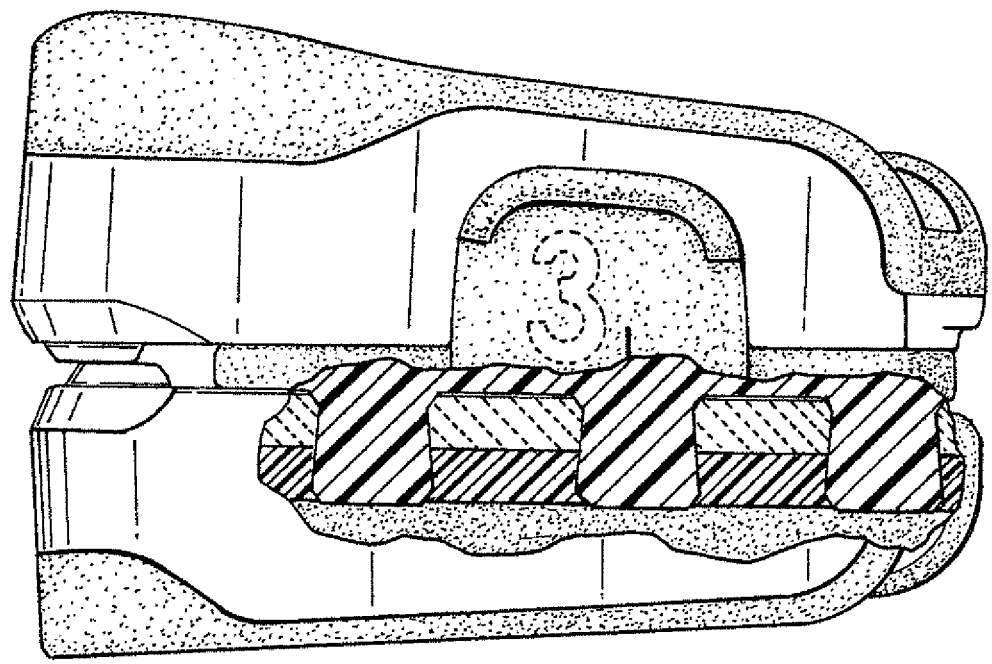
Figure 5C:
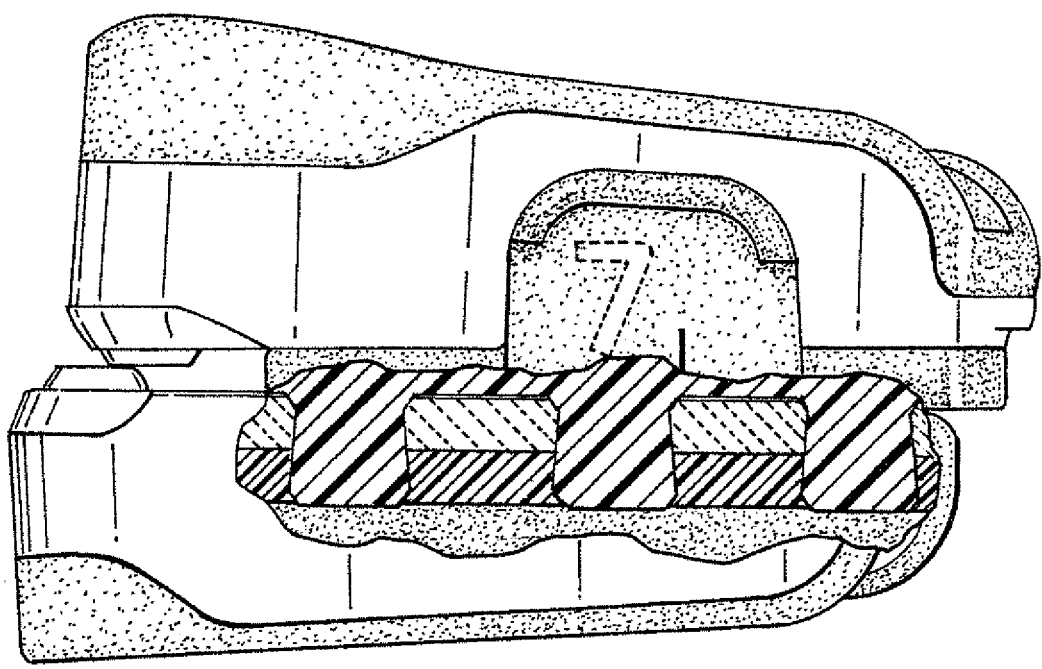

Turning next to FIGS. 5a-c, shown are partial cut-away side views of the oral appliance shown in FIGS. 1-4 depicted in each of a first configuration 24, a second configuration 26 and a third configuration 28 to show various applications of the oral appliance 10 and the progression of overbite orientations using a plurality different adjustment plates or spacers 14a/14b. As first seen in FIG. 5a, configuration 24 utilizes, for example, spacers 14a/14b having a first configuration of connecting pegs 18a/18b such that the oral appliance 10 is configured for a user having an over-bite where the upper body member 12a extends forward of the lower body member 12b. Following use of such a first configuration 24 of the oral appliance 10 for a period of time, the user may then be directed to advance to a second configuration (not shown), and then to a third configuration 26 as seen in FIG. 5b, where the upper and lower body members 12a/12b are more closely aligned. Following further use of the oral appliance 10, the user may be directed to then use a fourth configuration (not shown) where the upper and lower body members 12a/12b are in substantial alignment.

Conversely, as seen in FIG. 5b, configuration 28 utilizes, for example, spacers 14a/14b having a seventh configuration of connecting pegs 18a/18b such that the oral appliance 10 is configured for a user having an under-bite where the lower body member 12b extends forward of the upper body member 12a, Following use of such a seventh configuration 28 of the oral appliance 10 for a period of time, the user may then be directed to advance to a sixth and then fifth configuration (not shown) where the upper and lower body members 12a/12b are more closely aligned. Then, as discussed above, following further use of the oral appliance 10, the user may be directed to then use a fourth configuration (not shown) where the upper and lower body members 12a/12b are in substantial alignment.

Figure 6:
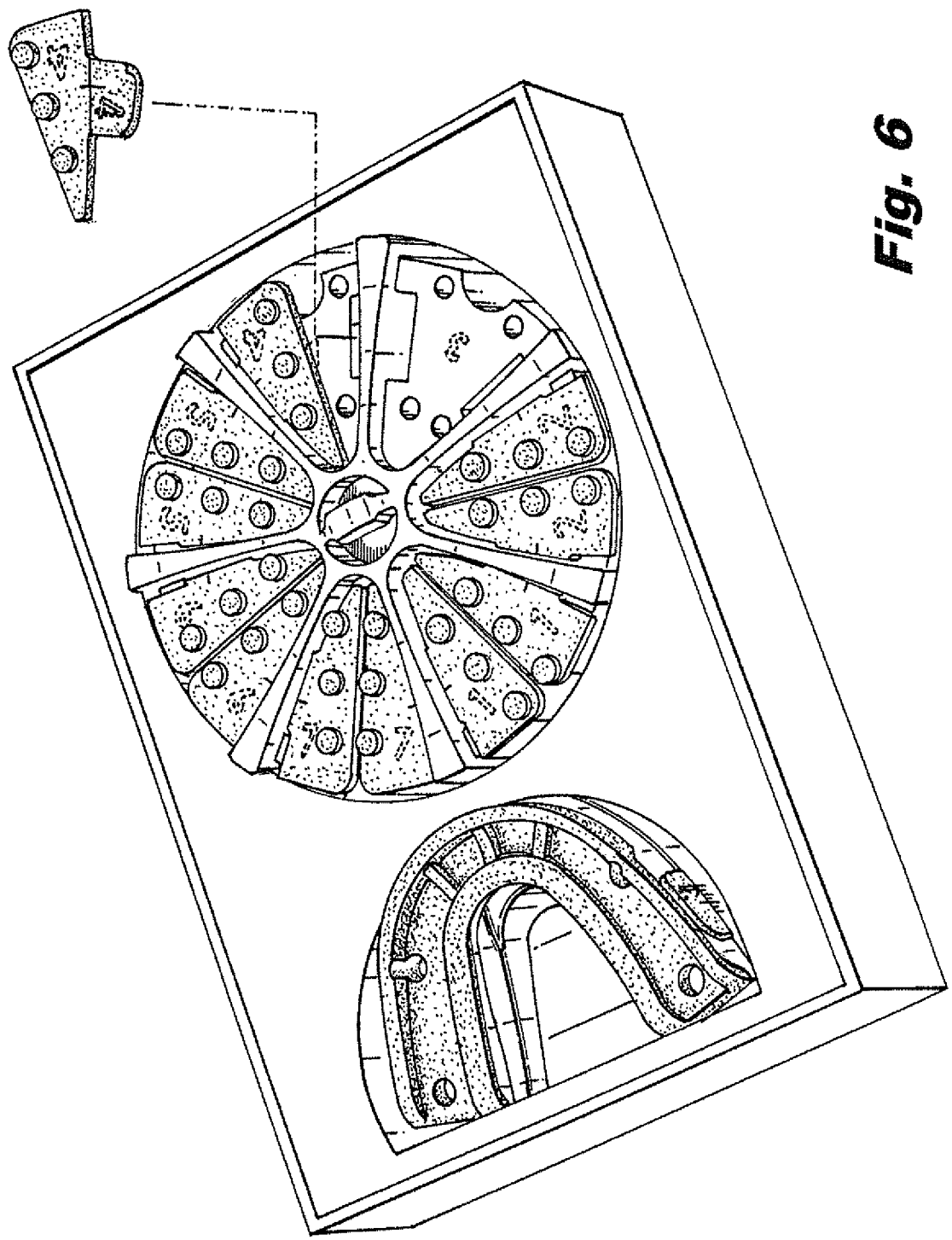
FIG. 6 shows a perspective view of an oral appliance kit in accordance with an exemplary embodiment of the present invention.

Referring last to FIG. 6, shown is a perspective view of an oral appliance kit 30 in accordance with an exemplary embodiment of the present invention. As shown, the kit 30 provides upper and lower members of an oral appliance 33 for correcting misalignment of a user's teeth or jaw. As depicted, the kit 30 preferably includes a storage container 32 having a plurality of cavities 31/34 for housing the first and second generally U-shaped body members of the oral appliance 33, and a plurality of pairs of adjustment plates or spacers 34a-g stored in a visibly accessible manner. The kit 30 is preferably configured to house spacers 34a-g in a manner that each is visibly accessible to a user for easy selection and replacement. Preferably, each pair of spacers 34a-g are arranged in a progressive configuration for the user such that the progression is readily identifiable through, for example, the use of identification indicia 35a-g. In one embodiment, spacers 34a-g may be maintained in a turret style housing having dividing walls 40 and an optional handle 38. For securing spacers 34a-g, the turret housing may have securing holes 37a-g (only 37c being visible) that correspond to the connecting pegs of the spacers 34a-g. Similarly, receiving holes 39a-g (only 36c-d being visible) are provided for receiving the side element of each of the spacers 34a-g. Other shapes and configurations for the storage housing for the kit 30 in accordance with the invention will be apparent and are considered within the scope of the present invention. That is, the oral appliance kit 30 may be oriented in various ways other than as shown, and spacers 34a-g may be linearly or vertically oriented, there may be more than 7 sizes may be employed, the kit 30 may employ 2 millimeter or 3 millimeter spacers 34a-g.

Also in accordance with the present invention, provided is a method for the correction of the misalignment of a person's teeth or jaw to alleviate tension and/or stress. Preferably, a first step provides an oral appliance having first and second generally U-shaped body members adapted to be positioned over at least a portion of first and second arches of teeth. The first step further includes providing one or more of each of first and second adjustment plates or spacers each having a plurality of connecting pegs on each of a first and second side thereof. Next, opposing contact surfaces of the first and second body members are connected using the first adjustment plate. Once connected, the oral appliance is placed or positioned between the upper and lower teeth of a user. After some time, the oral appliance is removed from the upper and lower teeth of the user, and the opposing contact surfaces of the first and second body members are disconnected from the first adjustment plate or plates. Next, selecting the second adjustment plate or plates, the opposing contact surfaces of the first and second body members are again connected using the second adjustment plate or plates to form a second oral appliance having a slightly different configuration from the oral appliance using the first adjustment plate. Finally, the second oral appliance is placed or positioned between the upper and lower teeth of the user for a second duration of time. This process can be repeated using as many of the different spacers as are necessary to achieve the desired result. Importantly, a difference between the different spacers is that the connecting pegs on a first adjustment plate are in a slightly different position from the connecting pegs on the second adjustment plate in order to cause a slightly altered relationship between the upper and lower body members during use of the different spacers.

REFERENCE NUMERALS marking indicia 1, 2
rigid material 3
softening material 4
air gap 5
spacer engagement slot 6
angled tongue side wall 8a, 8b
oral appliance 10
upper member 12a
lower member 12b
upper teeth channel 13a
lower teeth channel 13b
adjustment plates or spacers 14a, 14b
spacer base plate 15a, 15b
spacer side element 16a, 16b
side element lip 17a, 17b
spacer pegs 18a, 18b
peg receiving holes 20a, 20b
upper and lower front spacers 22a, 22b
spacer adjustment number 24, 26, 28
oral appliance kit 30
appliance storage cavity 31
kit container body 32
upper/lower members 33
spacer storage turret 34
adjustment spacer set 34a-g
spacer identification indicia 35a-g 36c
peg receiving holes 37c
spacer storage turret central holding element 38
side element receiving hole 39c
turret dividing wall 40

In the claims, means or step-plus-function clauses are intended to cover the structures described or suggested herein as performing the recited function and not only structural equivalents but also equivalent structures. Thus, for example, although a nail, a screw, and a bolt may not be structural equivalents in that a nail relies on friction between a wooden part and a cylindrical surface, a screw's helical surface positively engages the wooden part, and a bolt's head and nut compress opposite sides of a wooden part, in the environment of fastening wooden parts, a nail, a screw, and a bolt may be readily understood by those skilled in the art as equivalent structures.

Having described at least one of the preferred embodiments of the present invention with reference to the accompanying drawings, it is to be understood that such embodiments are merely exemplary and that the invention is not limited to those precise embodiments, and that various changes, modifications, and adaptations may be effected therein by one skilled in the art without departing from the scope or spirit of the invention as defined in the appended claims. The scope of the invention, therefore, shall be defined solely by the following claims. Further, it will be apparent to those of skill in the art that numerous changes may be made in such details without departing from the spirit and the principles of the invention. It should be appreciated that the present invention is capable of being embodied in other forms without departing from its essential characteristics.

What is claimed is:

1. An oral appliance, comprising:
first and second generally U-shaped body members adapted to be positioned over at least a portion of first and second arches of teeth, wherein said first and second body members each have a plurality of connecting holes on an opposed pair of contact surface thereof;
each of the generally U-shaped body members comprising both a rigid portion and a moldable portion, the moldable portion overlaying the rigid portion and being configured to mold to respective ones of the at least a portion of first and second arches of a user's teeth during a use;
an exterior surface of each of the first and second U-shaped body members comprises the generally horizontal contact surface contiguously coupled to first and second generally vertical side surfaces forming an interior channel therein, wherein the first vertical side surface is adapted to correspond to a front surface of one of the first or second arches of teeth and the second vertical side surface is adapted to correspond to a back surface of the first or second arches of teeth, the interior channel of the U-shaped body generally conforming to a shape of the first or second arches of teeth;
a pair of recesses, each of the pair of recesses disposed and extending partially along a side wall of either the first or second U-shaped body member, and orthogonally positioned with respect to said contact surfaces, and each, disposed proximate a midpoint between a distal end and a proximal end of at least one of the first and second body members;
a first spacing protrusion at a first nadir disposed on a bottom planar surface of the first body member;
a second spacing protrusion at a second nadir disposed on an upper planar surface of the second body member, the first and the second spacing protrusion being configured to rest against one another and define a front air gap between a front region of the first and second body members during a contact therebetween;
angled inner surfaces on the first and second body members being configured to guide the user's tongue toward a position that minimizes interference with breathing;
a tongue training reflex contact disposed on said angled inner surface of said first body member, said tongue training reflex contact extending outwardly from said angled inner surface of said first body member;
at least a pair of repositionable spacing elements removably disposed on said opposed contact surfaces of each of said first and second U-shaped body members proximate said midpoint;
each said spacing elements each further comprise a generally flat base plate and a side latching element positioned perpendicularly to said flat base plate;
a plurality of connecting pegs positioned on each of a first and a second side of said base plate and projecting a distance from said base plate;
each of the connecting pegs having a width that tapers from its distal end toward said base plate, each of the plurality of connecting holes being adapted to removably receive at least one of the connecting pegs in a snap-fit connection;
and said side latching elements each configured with respect to said base plate in a snap-fit engagement, the side latching element being removably receivable within a corresponding one of the pair of recesses, wherein each of the at least a pair of repositionable spacing elements is configured to correspond to one relative positioning of the first and second body members with respect to one another;
wherein the first and second generally U-shaped body members are lockable both translatable and pivotably with respect to one another by said spacing elements but are not hingably attached and not are movable relative to each other in a locked condition during said use;
wherein the spacing element is selectable amongst a plurality of spacing elements that have differing configurations of pegs such that a desired locked arrangement of the first and second generally U-shaped body members with respect to one another is determinable based on the selected spacing element; and
wherein the spacing element including the side latching element that is receivable within said recess of said side wall and is perpendicular to said base plate so that said spacing element engages respective said U-shaped body members in two perpendicular directions.

2. The oral appliance according to claim 1, wherein the moldable portion comprises a material selected from the group consisting of a flexible polymeric material, a flexible ethylene material, a rigid polymeric material, and a polymerizable acrylic compound.

3. The oral appliance according to claim 1, wherein said generally U-shaped body members comprise a material that is capable of being molded to conform to a shape of a dental arch of a patient with the application of heat.

4. The oral appliance according to claim 1, wherein the moldable portion comprises a flexible heat responsive polymeric material that shapes to a user's first or second arch of teeth in response to heating and then cooling the U-shaped body member.

5. An oral appliance comprising:
first and second generally U-shaped body members adapted to be positioned over at least a portion of first and second arches of teeth, wherein each of said body members comprises a portion of rigid material and a portion of flexible material and said first and second body members each have a plurality of connecting holes on a contact surface;
an exterior surface of each of the first and second U-shaped body members comprises the contact surfaces contiguously coupled first and second generally vertical side surfaces forming an interior channel therein, wherein the first vertical side surface is adapted to correspond to a front surface of one of the first or second arches of teeth and the second vertical side surface is adapted to correspond to a back surface of the first or second arches of teeth, the interior channel of the U-shaped body generally conforming to a shape of the first or second arches of teeth, and wherein said contact surfaces are connected with an at least one adjustment plate;
a pair of recesses disposed in and extending partially in a side wall of either the first or second U-shaped body member, orthogonally positioned with respect to biting surfaces, that is disposed between a distal end and a proximal end of at least one of the first and second body members;
a first spacing protrusion at a first nadir of the first body member;
a second spacing protrusion at a second nadir of the second body member, the first and the second spacing protrusion being configured to rest against one another and define a front air gap between a front region of the first and second body members;
angled inner surfaces on the first and second body members being configured to guide the user's tongue toward a position that minimizes interference with breathing;
a tongue training reflex contact disposed on said angled inner surface of said first body member, said tongue training reflex contact extending outwardly from said angled inner surface of said first body member;
said at least one adjustment plate having at least two connecting pegs for repositionably connecting opposing surfaces of said first and second body members, the at least one adjustment plate positioned perpendicularly to a respective side latching element; and
each side latching element being at least partially received within a corresponding one of the recesses, the at least one adjustment plate being configured to secure the first and second body members at a single relative positioning relative to one another when the first and second body members engage one another; and
wherein each of the connecting pegs has a width that tapers from its distal end toward said base plate, each of the plurality of connecting holes being adapted to removably receive at least one of the connecting pegs in a snap-fit connection;
wherein the first and second generally U-shaped body members are lockable both translatably and pivotably with respect to one another by said spacing elements and not movable relative to each other in a locked condition during said use;
wherein the at least one adjustment plate is selectable amongst a plurality adjustment plates that have differing configurations of pegs such that a desired locked arrangement of the first and second generally U-shaped body members with respect to one another is determinable based on the selected at least one adjustment plate; and
wherein the at least one adjustment plate includes a protruding side element that is receivable within said recess of said side wall and perpendicular to each of said adjustment plate thereby securing said adjustment plate simultaneously in two orientations.

6. The oral appliance according to claim 5, wherein at least a portion of the first and second U-shaped body members comprises a material selected from the group consisting of a flexible polymeric material, a flexible ethylene material, a polymerizable acrylic compound, and a rigid polymeric material.

7. The oral appliance according to claim 5, wherein said generally U-shaped body members comprise a material that is capable of being molded to conform to a shape of a dental arch of a patient with the application of heat.

8. The oral appliance according to claim 5, wherein at least a portion of the first and second U-shaped body members comprises a flexible heat responsive polymeric material that shapes to a user's first or second arch of teeth in response to heating and then cooling the U-shaped body member.

9. The oral appliance according to claim 5, wherein the first or second body member has a lateral width in the range of substantially 1 inch and substantially 2.5 inches.

10. The oral appliance according to claim 5, wherein the first or second body member has a longitudinal length in the range of substantially 2 inch and about 3 inches.

11. The oral appliance according to claim 5, wherein the first or second body member has a height thickness in the range of substantially 0.25 inch and substantially 0.75 inch.

12. The oral appliance according to claim 5, wherein the first or second body member has a lateral width of substantially 1.75 inches.

13. The oral appliance according to claim 5, wherein the first or second body member has a longitudinal length of substantially 2.5 inches.

14. The oral appliance according to claim 5, wherein the first or second body member has a height thickness of substantially 0.5 inch.

15. The oral appliance according to claim 5, wherein the first or second body member has a height thickness of substantially 0.65 inch.

16. The oral appliance according to claim 5, further comprising a plurality of pairs of adjustment plates, each pair of adjustment plates comprising connecting pegs positioned in different locations on said base plates.

17. An oral appliance assembly, comprising:
first and second molded body members each body member comprising a contact surface and a pair of side walls orthogonally positioned with respect to biting surfaces, each of the side walls of either the first or second body member forming one of a pair of recesses therein disposed between a distal end and a proximal end of each of the side walls, the recesses extending partially through each of the side walls, wherein said first and second molded body members each has a plurality of connecting holes on a contact surface thereof;
a first spacing protrusion at a first nadir of the first body member;
a second spacing protrusion at a second nadir of the second body member, the first and the second spacing protrusion being projecting opposed to each other and configured to rest against one another and define a front air gap between a front region of the first and second body members;
angled inner surfaces on the first and second body members being configured to guide the user's tongue toward a position that minimizes interference with breathing;
a tongue training reflex contact disposed on said angled inner surface of said first body member, said tongue training reflex contact extending outwardly from said angled inner surface of said first body member;
at least a pair of spacing elements configured so as to be repositionably interconnected between contact surfaces of said molded body members, each of the spacing elements being received within a corresponding one of the recesses to secure the at least one spacing element at a fixed position within a respective one of the recesses; and
wherein each of the pair of spacing elements additionally extends perpendicular to a side latching element and further comprises a generally flat base plate, a plurality of connecting pegs positioned on each of a first and second side of said base plate and project a distance from said base plate, each of the connecting pegs has a width that tapers from its distal end toward said base plate, each of the plurality of connecting holes being adapted to removably receive at least one of the connecting pegs in a snap-fit connection;

wherein the first and second molded body members are lockable both translatably and pivotably with respect to one another by said spacing elements;

wherein the spacing element is selectable amongst a plurality of spacing elements that have differing configurations of pegs such that a desired locked arrangement of the first and second generally U-shaped body members with respect to one another is determinable based on the selected spacing element; and wherein each of said spacing elements further including a protruding side element that is lockably received within a respective one of said recesses of said side wall thereby engaging between first and second molded body members in two different orientations at the same time.

18. A kit for providing an oral appliance for correcting misalignment of a user's teeth or jaw to alleviating tension and/or stress, wherein said kit comprises:

a storage container having a plurality of cavities for housing an oral appliance;

first and second generally U-shaped body members of said oral appliance, at least one of the first and second body members including a side wall, orthogonally positioned with respect to biting surfaces, the first or second U-shaped body member having a pair of recesses, each recess extending partially therethrough at a location disposed between a distal end and a proximal end of the at least one of the first and second body members;

a first spacing protrusion at a first nadir of the first body member;

a second spacing protrusion at a second nadir of the second body member, the first and the second spacing protrusion being configured to rest against one another and define a front air gap between a front region of the first and second body members;

angled inner surfaces on the first and second body members being configured to guide the user's tongue toward a position that minimizes interference with breathing;

a tongue training reflex contact disposed on said angled inner surface of said first body member, said tongue training reflex contact extending outwardly from said angled inner surface of said first body member;

a plurality of pairs of adjustment spacers stored in a visibly accessible manner, each of the adjustment plates or spacers being configured to be received within a corresponding one of the recesses, each of the adjustment spacers being configured to secure the first and second body members at a relative positioning relative to one another when the first and second body members engage one another; and wherein said first and second U-shaped body members each has a plurality of connecting holes on a contact surface thereof, each of said adjustment spacers comprise a generally flat base plate, a plurality of connecting pegs positioned on each of a first and second side of said base plate and project a distance from said base plate, each of the connecting pegs has a width that tapers from its distal end toward said base plate, each of the plurality of connecting holes being adapted to removably receive at least one of the connecting pegs in a snap-fit connection;

wherein the first and second generally U-shaped body members are lockable both translatably and pivotably with respect to one another by said spacing elements and not are movable relative to each other in a locked condition;

wherein the spacing element is selectable amongst a plurality of provided spacing elements that have differing configurations of pegs such that a desired locked arrangement of the first and second generally U-shaped body members with respect to one another is determinable based on the selected spacing element; and wherein each of said spacing elements further including a protruding side element that is lockably received within a respective one of said recesses of said side wall thereby engaging between first and second molded body members in two different orientations at the same time.

19. The kit according to claim 18, wherein said generally U-shaped body members have opposing upper and lower planar surfaces, the body members comprising a material that is capable of being molded to conform to a shape of a dental arch of a patient with the application of heat.

20. The kit according to claim 18, wherein the body members comprise a material selected from the group consisting of a flexible polymeric material, a flexible ethylene material, a rigid polymeric material, and a polymerizable acrylic compound.

21. A method for improving the alignment of a user's jaw and related anatomical structures for enhanced airway function: comprising the steps of:

providing an oral appliance, comprising:
first and second generally U-shaped body members adapted to be positioned over at least a portion of first and second arches of teeth, one of the first and second body members including a pair of recesses, each recess extending partially through a location between a proximal end and a distal end of a side wall, orthogonally positioned with respect to biting surfaces, of the at least one of the first and second body members;

a first spacing protrusion at a first nadir of the first body member;

a second spacing protrusion at a second nadir of the second body member, the first and the second spacing protrusion being configured to rest against one another and define a front air gap between a front region of the first and second body members;

angled inner surfaces on the first and second body members being configured to guide the user's tongue toward a position that minimizes interference with breathing;

a tongue training reflex contact disposed on said angled inner surface of said first body member, said tongue training reflex contact extending outwardly from said angled inner surface of said first body member; and providing first and second adjustment plates, the first and second adjustment plates being removably receivable in a corresponding one of the recesses, each of the first and second adjustment plates having at least two connecting pegs on each of a first and second side thereof, the first and second adjustment plates securing the at least two pegs at a fixed position;

connecting opposing contact surfaces of said first and second body members with said first adjustment plate;

placing said oral appliance between upper and lower teeth of a user;

removing said oral appliance from said upper and lower teeth of a user;

disconnecting said opposing contact surfaces of said first and second body members from said first adjustment plate;
connecting opposing contact surfaces of said first and second body members with said second adjustment plate to form a second oral appliance; and
placing said second oral appliance between upper and lower teeth of a user,
wherein at least one of said connecting pegs on said first adjustment plate is in different position from at least one of said connecting pegs on said second adjustment plate, wherein said first and second U-shaped body members each has a plurality of connecting holes on a contact surface thereof, each of said adjustment plates or spaces comprise a generally flat base plate, a plurality of connecting pegs positioned on each of a first and second side of said base plate and project a distance from said base plate, each of the connecting pegs has a width that tapers from its distal end toward said base plate, each of the plurality of connecting holes being adapted to removably receive at least one of the connecting pegs in a snap-fit connection; and
wherein each of said spacing elements further including a protruding side element that is lockably received within respective recesses of said side wall thereby engaging between first and second molded body members in two different orientations at the same time.

* * * * *